United States Patent [19]

Robbins

[11] 4,415,503

[45] Nov. 15, 1983

[54] METHOD FOR PREPARATION OF N-PHOSPHONOMETHYLGLYCINE

[75] Inventor: Jeffrey D. Robbins, Berkeley, Calif.

[73] Assignee: Stauffer Chemical Company, Westport, Conn.

[21] Appl. No.: 424,941

[22] Filed: Sep. 28, 1982

[51] Int. Cl.³ ............................................. C07F 9/38
[52] U.S. Cl. ............................................. 260/502.5 F
[58] Field of Search .................. 260/502.5 F, 502.5 E

[56] References Cited

U.S. PATENT DOCUMENTS

| | | | |
|---|---|---|---|
| 2,847,442 | 8/1958 | Sallmann | 260/502.5 E |
| 3,288,846 | 11/1966 | Irani et al. | 260/502.5 F |
| 3,366,677 | 1/1968 | Quimby | 260/502.4 A |
| 3,547,728 | 12/1970 | Balde et al. | 260/502.5 E |
| 3,832,393 | 8/1974 | Krueger et al. | 260/502.5 E |
| 4,053,505 | 10/1977 | Dutra | 260/502.5 F |
| 4,235,809 | 11/1980 | Redmore | 546/21 |

FOREIGN PATENT DOCUMENTS

| | | | |
|---|---|---|---|
| 2131017 | 12/1972 | Fed. Rep. of Germany | 260/502.5 E |
| 141929 | 5/1980 | German Democratic Rep. | 260/502.5 F |
| 1445087 | 8/1976 | United Kingdom | 260/502.5 F |

Primary Examiner—J. E. Evans
Attorney, Agent, or Firm—Paul R. Martin

[57] ABSTRACT

Disclosed is a method for the preparation of N-phosphonomethylglycine which comprises the steps of (a) reacting 1,3,5-tri-(substituted methyl) hexahydro-s-triazine, a compound of the formula

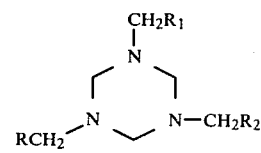

wherein R, $R_1$ and $R_2$ are the same or different and are selected from the group consisting of cyano, alkoxycarbonyl wherein the alkyl group ranges from 2 to 18 carbon atoms, and aryloxycarbonyl wherein the aryl group ranges from 6 to 12 carbon atoms, with a substituted phosphorus compound having the formula PXYZ wherein X is a halogen, Y and Z are each independently selected from the group consisting of halogen, alkoxy having from 1 to 10 carbon atoms and aryloxy, in the presence of a low molecular weight carboxylic acid solvent and a protic acid; (b) treating the reaction mixture with water; (c) removing said solvent and hydrolyzing the residue with aqueous alkali to generate a salt of N-phosphonomethylglycine; and (d) neutralizing said salt with an acid to produce the end product, N-phosphonomethylglycine.

8 Claims, No Drawings

METHOD FOR PREPARATION OF N-PHOSPHONOMETHYLGLYCINE

BACKGROUND OF THE INVENTION

This invention relates to a novel method for the preparation of N-phosphonomethylglycine, a compound which is a known herbicide and plant growth regulator.

Herbicides are widely used by farmers, commercial agricultural companies, and other industries in order to increase crop yields for such staple crops as corn, soybeans, rice, and the like, and to eliminate weed growth along highways, railroad rights-of-way, and other areas. Herbicides are effective in killing or controlling unwanted weeds which compete for soil nutrients with the crop plants, and by reason of the fact that they kill weeds, are responsible for improving the aesthetic appearance of highway and railroad rights-of-way. There are a number of different types of herbicides presently sold commercially, and these fall into two general categories. The categories are pre-emergence and post-emergence herbicides. The pre-emergence herbicides are incorporated into the soil prior to the emergence of the weed plants from the soil, and the post-emergence herbicides are applied to plant surfaces after emergence of the weeds or other unwanted plants from the soil.

One of the earliest post-emergence herbicides used commercially was 2,4-D (2,4-dichlorophenoxyacetic acid). After a number of years of use of this and similar compounds such as 2,4,5-T (2,4,5-trichlorophenoxy acetic acid), it was found that certain decomposition products of these herbicides were long lasting and were not biodegradable. While there has been some dispute between governmental agencies and commercial interests regarding the effects of residual products of 2,4-D, 2,4,5-T and similar compounds, the agencies nevertheless restricted the use of these herbicides in the United States some years ago. Since that time, efforts have been made to develop herbicides which are biodegradable into harmless residues within a relatively short time after their application.

One such compound, which has been found to be biodegradable, yet which is effective as a herbicide and plant growth regulator when employed at lower rates, is N-phosphonomethylglycine and various salts thereof. N-Phosphonomethylglycine and agriculturally effective salts have been approved for use by the U.S. Government, and, as a consequence, this herbicide has become extremely successful commercially.

N-Phosphonomethylglycine and certain salts are the only effective and approved post-emergence herbicides in the field. The present commercial compound is the isopropylamine salt of N-phosphonomethylglycine and derivatives thereof.

In field use it is normally applied in amounts of from 0.01 to about 20 pounds per acre, preferably from 2 to 6 pounds per acre.

N-Phosphonomethylglycine, and certain soluble salts thereof, can be made in a number of different ways. One such method, as described in U.S. Pat. No. 3,160,632 (Toy et al., Dec. 8, 1964) is to react N-phosphinomethylglycine (glycinemethylenephosphonic acid) with mercuric chloride in a water solvent at reflux temperature, and subsequently separating the reaction products. Another method is the reaction of ethyl glycinate with formaldehyde and diethylphosphite. The latter method is described in U.S. Pat. No. 3,799,758 (Franz, Mar. 26, 1974). In addition, there is a whole series of patents, relating to N-phosphonomethylglycine, its salts, and derivatives thereof, described as being useful herbicides and plant growth regulators. Such additional patents relating to N-phosphonomethylglycine, methods of application, methods of preparation, salts, and derivatives, include U.S. Pat. No. 3,868,407, U.S. Pat. No. 4,197,254, and U.S. Pat. No. 4,199,354, among others.

Because of the importance of N-phosphonomethylglycine and certain salts as a herbicide, other methods of making the compounds are constantly being sought in order to provide improved or alternate methods of manufacture.

SUMMARY OF THE INVENTION

It has now been discovered that N-phosphonomethylglycine can be produced by:

(a) reacting 1,3,5-tri-(substituted methyl)hexahydro-s-triazine, a compound of the formula

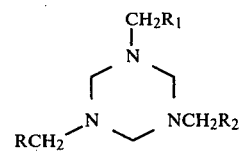

wherein R, $R_1$ and $R_2$ are the same or different and are selected from the group consisting of cyano, alkoxycarbonyl wherein the alkyl group ranges from 2 to 18 carbon atoms, and aryloxycarbonyl wherein the aryl group ranges from 6 to 12 carbon atoms, with a substituted phosphorus compound having the formula PXYZ wherein X is a halogen, Y and Z are each independently selected from the group consisting of halogen, alkoxy having from 1 to 10 carbon atoms and aryloxy, in the presence of a low molecular weight carboxylic acid solvent and a protic acid;

(b) treating the reaction mixture with water;

(c) removing said solvent and hydrolyzing the residue to generate a salt of N-phosphonomethylglycine; and (d) neutralizing said salt to produce the end product, N-phosphonomethylglycine.

The preferred starting compound for use in the process of the invention is 1,3,5-tri-(cyanomethyl)hexahydro-s-triazine. Other substituted hexahydro-triazine compounds can be used, such as 1,3,5-tris(alkoxycarbonylmethyl)-hexahydro-s-triazine or 1,3,5-tris(aryloxycarbonylmethyl)hexahydro-s-triazine.

Acetic acid is the preferred low molecular weight carboxylic acid for use in step (a) of the process of the invention. Other suitable low molecular weight carboxylic acids which can be used for solvent purposes include propanoic acid and butanoic acid, for example.

Preferred substituted phosphorus compounds for use in the above process include phosphorus trichloride, phosphorus tribromide, ethyl dichlorophosphite, and diethylchlorophosphite. Most preferred is phosphorus trichloride.

Suitable protic acids include hydrogen chloride, hydrogen bromide, sulfuric acid, and hydrogen iodide.

Step (c), the hydrolyzing of the residue, is preferably carried out with the use of aqueous alkali. The preferred base for use in step (c) of the process is sodium hydroxide, however, other alkali or alkaline earth hydroxides such as potassium hydroxide can also be used.

The neutralization of the salt in step (d) is preferably carried out with a strong acid. The preferred acid for use in step (d) of the process of the invention is hydrochloric acid. However, other acids such as hydrobromic acid, hydriodic acid, sulfuric acid, and phosphoric acid, can be used. These acids may be described as relatively strong protic acids and any other acids falling within that purview would be suitable for use also.

Alternatively, the hydrolysis of step (c) may be affected in refluxing aqueous acid, for example, hydrochloric acid. When hydrolysis is accomplished in this manner, an acid salt of N-phosphonomethylglycine is formed. The final product, N-phosphonomethylglycine, is then obtained by neutralization with a suitable base, e.g. sodium hydroxide.

Using the preferred compounds, the overall reaction for the process of the invention can be represented as follows:

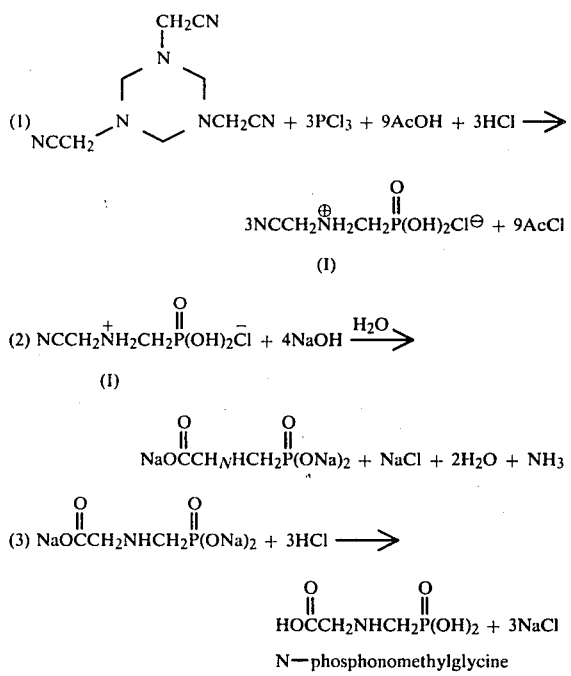

The formation of N-phosphonomethylglycinonitrile (I) according to Equation 1 is believed to occur, but it has not yet been demonstrated that this compound is truly an intermediate.

This invention will be better understood by reference to the specific example which follows, which serves to illustrate the instant invention.

EXAMPLE I

Preparation of N-Phosphonomethylglycine

Into a 100 milliliter (ml), three-necked, round-bottomed flask equipped with a magnetic stirrer, a nitrogen bubbler, a thermometer, dropping funnel, gas inlet tube, and an ice bath was charged 4.1 grams (g) (0.030 mole) of phosphorus trichloride and 10 ml acetic acid. This mixture was cooled to 10° C. The solution became cloudy, and at that point the sub-surface addition of hydrogen chloride was begun. After 5 minutes, 2.0 g (0.054 mole) of hydrogen chloride had been added. Then, as HCl addition was continued, a solution of 2.0 g (0.010 mole) of 1,3,5-tri(cyanomethyl)hexahydro-s-triazine in 60 ml of acetic acid was added over 0.7 hours at 10°-15° C. Yellowish solids formed in the solution in the round-bottom flask after about ½ of the triazine had been added. At the end of the triazine and hydrogen chloride addition, the reaction mixture contained white solids. The reaction mixture was stirred overnight at ambient temperature. Water (5.0 ml) was then added dropwise, with cooling, at less than 31° C., and the mixture was stirred until all solids had dissolved. The reaction mixture was then stripped under mechanical vacuum at 40° C.

The pink oil obtained was dissolved in 5 ml of water and to this was added sufficient sodium hydroxide to raise the pH of the solution to 12. To this solution was added 8 ml of 10 N NaOH. The resulting solution was heated at reflux for six hours, cooled and analyzed by $^{13}C$ nmr, which indicated that N-phosphonomethylglycine was present (as its trisodium salt). The yield of the trisodium salt of N-phosphomethylglycine was measured by high performance liquid chromatography (anion exchange) and found to be 39% of the theoretical yield.

The trisodium salt of N-phosphonomethylglycine produced in accordance with the example above, can be converted to N-phosphonomethylglycine by addition of acid.

It will be recognized by those skilled in the art that variations in the quantities of reactants, temperatures used, mole ratios used, and time of reaction can be made in the method of the invention without departing from the spirit and scope of the appended claims.

What is claimed is:

1. A method for the preparation of N-phosphonomethylglycine which comprises the steps of:
   (a) reacting 1,3,5-tri-(substituted methyl)hexahydro-s-triazine, a compound of the formula

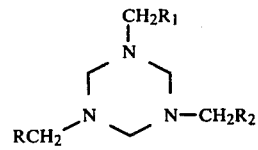

wherein R, $R_1$ and $R_2$ are the same or different and are selected from the group consisting of cyano, alkoxycarbonyl wherein the alkyl group contains from 2 to 18 carbon atoms, and aryloxycarbonyl wherein the aryl group ranges from 6 to 12 carbon atoms, with a substituted phosphorus compound having the formula PXYZ wherein X is a halogen, Y and Z are each independently selected from the group consisting of halogen, alkoxy having from 1 to 10 carbon atoms and aryloxy, in the presence of a low molecular weight carboxylic acid solvent and a protic acid;
   (b) treating the reaction mixture with water;
   (c) removing said solvent and hydrolyzing the residue to generate a salt of N-phosphonomethylglycine; and
   (d) neutralizing said salt to produce the end product, N-phosphonomethylglycine.

2. The method of claim 1 in which said substituted phosphorus compound is selected from the group consisting of phosphorus trichloride, phosphorus tribromide, ethyldichlorophosphite, and diethylchlorophosphite.

3. The method of claim 1 in which said low molecular weight carboxylic acid is selected from the group consisting of acetic, propanoic, and butanoic acid.

4. The method of claim 1 in which said triazine and substituted phosphorus compound of the formula PXYZ are used in approximately stoichiometric amounts and said carboxylic acid is used in excess.

5. The method of claim 1 in which said triazine is 1,3,5-tri(cyanomethyl)hexahydro-s-triazine.

6. The method of claim 1 in which said carboxylic acid is used in excess relative to said triazine.

7. The method of claim 1 in which the hydrolysis step (c) is carried out in aqueous acid an the neutralization step (d) is carried out with aqueous base.

8. The method of claim 1 in which the hydrolysis step (c) is carried out with an aqueous alkali base and the neutralization step (d) is carried out with an aqueous acid.

* * * * *

UNITED STATES PATENT AND TRADEMARK OFFICE
CERTIFICATE OF CORRECTION

PATENT NO. :   4,415,503
DATED      :   November 15, 1983
INVENTOR(S) :  Jeffrey D. Robbins It is certified that error appears in the above-identified patent and that said Letters Patent is hereby corrected as shown below:

In column 1, at line 62, the word "glycinemethylenephosphonic" should read --- glycinemethylenephosphinic ---.

Signed and Sealed this

Twentieth Day of November 1984

[SEAL]

Attest:

GERALD J. MOSSINGHOFF

Attesting Officer

Commissioner of Patents and Trademarks